United States Patent
Lee et al.

(10) Patent No.: US 10,067,067 B2
(45) Date of Patent: Sep. 4, 2018

(54) SUBSTRATE INSPECTION APPARATUS

(71) Applicant: Samsung Electronics Co., Ltd., Suwon-si, Gyeonggi-do (KR)

(72) Inventors: Seongsil Lee, Hwaseong-si (KR); Jeongho Ahn, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 30 days.

(21) Appl. No.: 15/203,317

(22) Filed: Jul. 6, 2016

(65) Prior Publication Data

US 2017/0067833 A1    Mar. 9, 2017

(30) Foreign Application Priority Data

Sep. 9, 2015 (KR) .................. 10-2015-0127757

(51) Int. Cl.
   *G01N 21/88*    (2006.01)
   *G01N 21/47*    (2006.01)
   *G01N 21/956*   (2006.01)

(52) U.S. Cl.
   CPC ....... *G01N 21/8806* (2013.01); *G01N 21/956* (2013.01); *G01N 2201/0636* (2013.01)

(58) Field of Classification Search
   CPC .................. G01N 21/88; G01N 21/47; G01N 2021/4735; G01N 2201/0636
   See application file for complete search history.

(56) References Cited

U.S. PATENT DOCUMENTS 5,018,865 A * 5/1991 Ferrell .................. B82Y 20/00
                                              250/227.11
5,465,145 A * 11/1995 Nakashige ............. G01N 21/94
                                              257/E21.53
(Continued)

FOREIGN PATENT DOCUMENTS

JP    2007/107960 A    4/2007
JP    2007/192560 A    8/2007
(Continued)

OTHER PUBLICATIONS

Lai Hock Tay et al., "Nanodomain Ca2+ of Ca2+ channels detected by a tethered genetically encoded Ca2+ sensor", nature communications, Apr. 10, 2012, pp. 1-11.
(Continued)

*Primary Examiner* — Sang Nguyen
(74) *Attorney, Agent, or Firm* — Harness, Dickey & Pierce, P.L.C.

(57) ABSTRACT

A substrate inspection apparatus may include a light source, which is configured to emit an incident light. The substrate inspection apparatus may further include a support, a detector, and a light adjuster. The supporting base configured to support a substrate, the detector configured to detect a defect on the substrate, and the light adjuster configured to allow the incident light to be reflected. The detector may be configured to collect a scattering signal. The scattering signal is generated from an optical interaction between an evanescent wave and the defect on the substrate, and to detect the defect. The evanescent wave may be generated when the incident light is totally and/or substantially reflected by the light adjuster.

19 Claims, 16 Drawing Sheets

(56) References Cited

U.S. PATENT DOCUMENTS

| | | | | |
|---|---|---|---|---|
| 5,774,221 | A * | 6/1998 | Guerra | G01J 9/00 356/4.01 |
| 5,939,709 | A * | 8/1999 | Ghislain | B82Y 20/00 250/216 |
| 6,545,276 | B1 * | 4/2003 | Sasaki | G01Q 60/22 250/216 |
| 7,158,224 | B2 * | 1/2007 | Montagu | G01N 21/0303 356/244 |
| 7,408,635 | B2 * | 8/2008 | Pobortchi | B82Y 20/00 356/301 |
| 8,269,969 | B2 | 9/2012 | Hayano | |
| 8,446,578 | B2 | 5/2013 | Sugihara et al. | |
| 8,695,110 | B2 * | 4/2014 | Nakata | G01Q 60/18 850/22 |
| 8,736,831 | B2 | 5/2014 | Ramachandran et al. | |
| 2006/0005615 | A1 * | 1/2006 | Ducker | B82Y 35/00 73/105 |
| 2006/0006317 | A1 * | 1/2006 | Itoh | B82Y 20/00 250/227.11 |
| 2007/0222440 | A1 * | 9/2007 | Komatsu | G01R 33/02 324/249 |
| 2008/0049236 | A1 * | 2/2008 | Iyoki | B82Y 35/00 356/614 |
| 2008/0246966 | A1 | 10/2008 | Oomori et al. | |
| 2012/0044346 | A1 | 2/2012 | Chou et al. | |
| 2012/0307605 | A1 * | 12/2012 | Zhang | G11B 5/455 369/13.32 |

FOREIGN PATENT DOCUMENTS

| | | |
|---|---|---|
| KR | 2001/0055184 A | 7/2001 |
| KR | 101446061 B1 | 10/2014 |

OTHER PUBLICATIONS

Alexa L. Mattheyses et al., "Imaging with total internal reflection fluorescence microscopy for the cell biologist", Journal of Cell Science 123 (21), Nov. 1, 2010, pp. 3621-3628.

* cited by examiner

CONVENTIONAL ART

SUBSTRATE INSPECTION APPARATUS

CROSS-REFERENCE TO RELATED APPLICATIONS

This U.S. non-provisional patent application claims priority under 35 U.S.C. § 119 to Korean Patent Application No. 10-2015-0127757, filed on Sep. 9, 2015, in the Korean Intellectual Property Office, the entire contents of which are hereby incorporated by reference.

BACKGROUND

The present disclosure relates to substrate inspection apparatuses, and in particular, to a substrate inspection apparatus configured to detect defects on substrates.

There is an ever increasing demand for high density semiconductor devices. As such, this demand leads to semiconductor devices with reduced sized patterns on the semiconductor devices, and an increased complexity of structure of the semiconductor devices. Accordingly, it may be useful to develop technologies that are capable of detecting defects in semiconductor devices. The defect-detection technologies may make it possible to improve reliability of a semiconductor device and as such increase the process yield of its fabrication process. An optical inspection technology is an example of one of the defect-detection technologies.

SUMMARY

Some example embodiments of inventive concepts provide substrate inspection apparatuses and optical inspection processes configured to reduce noise produced from any other region, other than an optical inspection region, and allowing a scattering signal to be extracted from a specific region of a substrate.

According to some example embodiments of inventive concepts, a substrate inspection apparatus may include a light source configured to emit an incident light, a support configured to support a substrate, a detector configured to detect a defect on the substrate based on a received scattering signal, and a light adjuster configured to reflect the incident light totally and/or substantially. The scattering signal is generated based on an optical interaction between an evanescent wave and the defect on the substrate. The evanescent wave may be generated when the incident light is totally and/or substantially reflected by the light adjuster.

In some example embodiments, the light adjuster may be spaced apart from a top surface of the substrate by a desired (and/or alternatively predetermined) distance. The distance may range from 150 nm (nanometer) to 300 nm. The evanescent wave may reach the top surface of the substrate but may not pass through the top surface.

In some example embodiments, the light adjuster may include a reflection prism.

In some example embodiments, the light adjuster may further include a moveable base for moving the reflection prism. The moveable base may be configured to move the reflection prism from an inspection position to a waiting position, the inspection position is when the reflection prism is between the substrate and the detector, and the waiting position is when the reflection prism is not between the substrate and the detector.

In some example embodiments, the substrate inspection apparatus may further include a controller, which is configured to extract information on the defect from the scattering signal. The controller may control the light adjuster to perform a first inspection process and a second inspection process. The first inspection process includes the reflection prism at the waiting position, and the second inspection process includes the reflection prism at the inspection position. The controller may be further configured to determine whether there is a first region within the defect during the first inspection process, the first region is an abnormal region which includes a size larger than a desired size. The controller may be further configured to perform the second inspection process on a second region of the substrate; the second region is different from the abnormal region.

In some embodiments, the light adjuster may include a light-condenser configured to reflect the incident light within the light-condenser; and a filter configured to remove a reflected fraction of the incident light.

In some example embodiments, the filter may include a transmissive part configured to have the incident light incident into an inner space of the light adjuster, and a filter part configured to limit and/or prevent propagation of the totally reflected fraction from the inner space to the light adjuster.

In some example embodiments, the filter may be provided in the filter part. The filter having a center spaced apart from a central axis of the inner space. The transmissive part may have a center on the central axis of the inner space, and the transmissive part configured to surround the filter.

In some example embodiments, the light source may include a first light source configured to emit a first incident light towards the substrate, and a second light source configured to emit a second incident light towards the light adjuster.

In some example embodiments, the substrate inspection apparatus may further include a controller, which is configured to control the light source and the light adjuster and to extract information on the defect, from the scattering signal collected by the light adjuster. The controller may control the light source and the light adjuster to perform a first inspection process and a second inspection process. The first inspection process may include emitting the first incident light to the substrate, and the second inspection process may include emitting the second incident light to the light adjuster.

In some example embodiments, under control of the control unit, the first inspection process may be performed to examine whether there is an abnormal region with a defect. The abnormal region having a size larger than a desired (and/or alternatively predetermined) size. The second inspection process may be performed on a region of the substrate, other than the abnormal region.

In some example embodiments, the controller may measure vertical positions of the top surface of the substrate and the light adjuster in the first inspection process, and may control the light adjuster to maintain the vertical positions during the second inspection process.

According to some example embodiments of inventive concepts, a substrate inspection apparatus may include a support configured to support a substrate; a light source configured to emit an incident light towards an inspection region of the substrate; a light adjuster including a reflector, the reflector positionable over the inspection region, and the reflector configured to allow the incident light to be totally and/or substantially reflected. The substrate inspection apparatus may further include a detector configured to collect a first scattering signal generated based on an optical interaction between an evanescent wave and a defect on the inspection region, the evanescent wave generated when the incident light is reflected. The substrate inspection apparatus may further include a controller configured to control the support, the light source, the light adjuster, and the detector. The controller may be configured to control the support and the light adjuster in such a way that the light adjuster is spaced apart from the substrate by a critical distance that is an effective reachable distance for the evanescent wave.

In some example embodiments, the controller may be configured to control the light source, the light adjuster, and the detector to perform a first inspection process and a second inspection process. The first inspection process is performed before the second inspection process. The controller may be configured to irradiate the inspection region with the incident light and collect a second scattering signal generated from an optical interaction between the incident light and the defect during the second inspection process. The controller may be configured to irradiate the total reflector with the incident light and collect the first scattering signal during the second inspection process.

In some example embodiments, the controller may determine whether there is a first region within the defect, the first region is an abnormal which includes a size is larger than a desired (and/or alternatively predetermined) size, based on the second scattering signal. The controller may further control the detector to exclude the abnormal region from the inspection region for the second inspection process.

In some example embodiments, a substrate inspection apparatus includes a reflection base may be positioned at a desired distance from a top surface of a substrate, the reflection base may be configured to produce an evanescent wave based on an incident light being reflected by a bottom surface of the reflection base, the evanescent wave may be configured to produce a scattering signal based on an optical interaction between the evanescent wave and a particle on the top surface. The evanescent wave may have optical characteristics which may depend on the desired distance between the reflection base and the top surface; the desired distance may be a target distance when intensity of the evanescent wave decreases by a desired factor.

The substrate inspection apparatus may further include a detector positionable above the reflection base; the detector is configured to detect a defect on the top surface based on the scattering signal. The reflection base may be connected to a light adjuster, the light adjuster may be positioned between the detector and the top surface, and the light adjuster may be configured to vertically adjust between a first position and a second position to obtain the desired distance. The substrate inspection apparatus may further include a controller coupled to the reflection base, the controller configured to extract information by processing the scattering signal.

BRIEF DESCRIPTION OF THE DRAWINGS

The foregoing and other features of inventive concepts will be more clearly understood and apparent from the more particular description of non-limiting embodiments of inventive concepts, as illustrated in the accompanying drawings in which like reference characters refer to like parts throughout the different views. The drawings are not necessarily to scale, emphasis instead being placed upon illustrating principles of inventive concepts. The drawings should not be interpreted as defining or limiting the range of values or properties encompassed by example embodiments. For example, the relative thicknesses and positioning of molecules, layers, regions and/or structural elements may be reduced or exaggerated for clarity. The accompanying drawings represent non-limiting, example embodiments as described herein. In the drawings.

DETAILED DESCRIPTION

Figure 1:
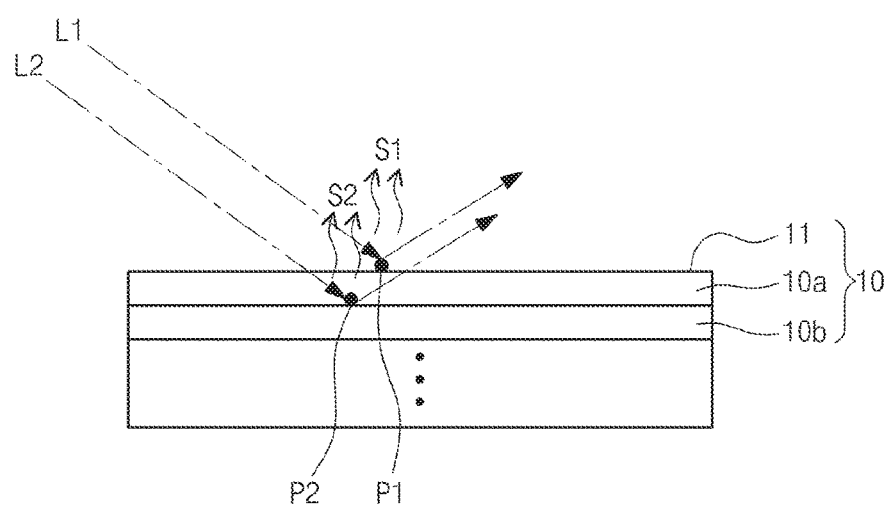
FIG. 1 is a diagram schematically illustrating a conventional optical inspection process to be performed on a substrate.

Example embodiments of inventive concepts will now be described more fully with reference to the accompanying drawings, in which example embodiments are shown. Example embodiments of inventive concepts may, however, be embodied in many different forms and should not be construed as being limited to the embodiments set forth herein; rather, these embodiments are provided so that this disclosure will be thorough and complete, and will fully convey the concept of example embodiments of inventive concepts to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an etched region or an implanted region illustrated as a rectangle may have rounded or curved features. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a diagram schematically illustrating a conventional optical inspection process to be performed on a substrate. An optical inspection process may be performed to detect a defect on a top surface 11 of a substrate 10. The optical inspection process may collect information (e.g., size and position) on the presence or absence of a defect, which may be created on the top surface 11 of the substrate 10. The defect may be characterized as, for example, including but not limited to, contaminants (e.g., particles) or abnormally-grown patterns may be categorized into a type of the defect.

Still referring to FIG. 1, light L1 and L2 may be incident on the top surface 11 of the substrate 10. The light L1 and L2 may include a first light L1 and a second light L2. Each of the first and second light L1 and L2 may be incident on edge regions of the substrate 10. The substrate 10 may include at least two layers (e.g., 10a and 10b). Accordingly, at least a fraction of the first and second light L1 and L2 may reach the layers 10a and 10b through the top surface 11 of the substrate 10. In some example embodiments, a first scattering signal S1 may be generated based on the optical interaction between the first light L1 and a first particle P1 on the top surface 11. The first scattering signal S1 contains information on the first particle P1, which may be collected by a detection unit (not shown).

Similarly, still referring to FIG. 1, a second scattering signal S2 containing may be generated from the optical interaction between a fraction of the second light L2 and a second particle P2 on the lower layer 10b. The second scattering signal S2 may contain information on the second particle P2. However, the second scattering signal S2 may lead to the difficulty in detecting a first defect, which may exist on the top surface 11 of the substrate 10. That is, for example, the second scattering signal S2 may serve as a noise, and thus not accurately detect the first defect on the top surface 11 of the substrate 10. In particular, when the substrate 10 has a multi-layered structure, an amount of such noise may be increased, and this may lead to deterioration in reliability of the optical inspection process.

Figure 2:
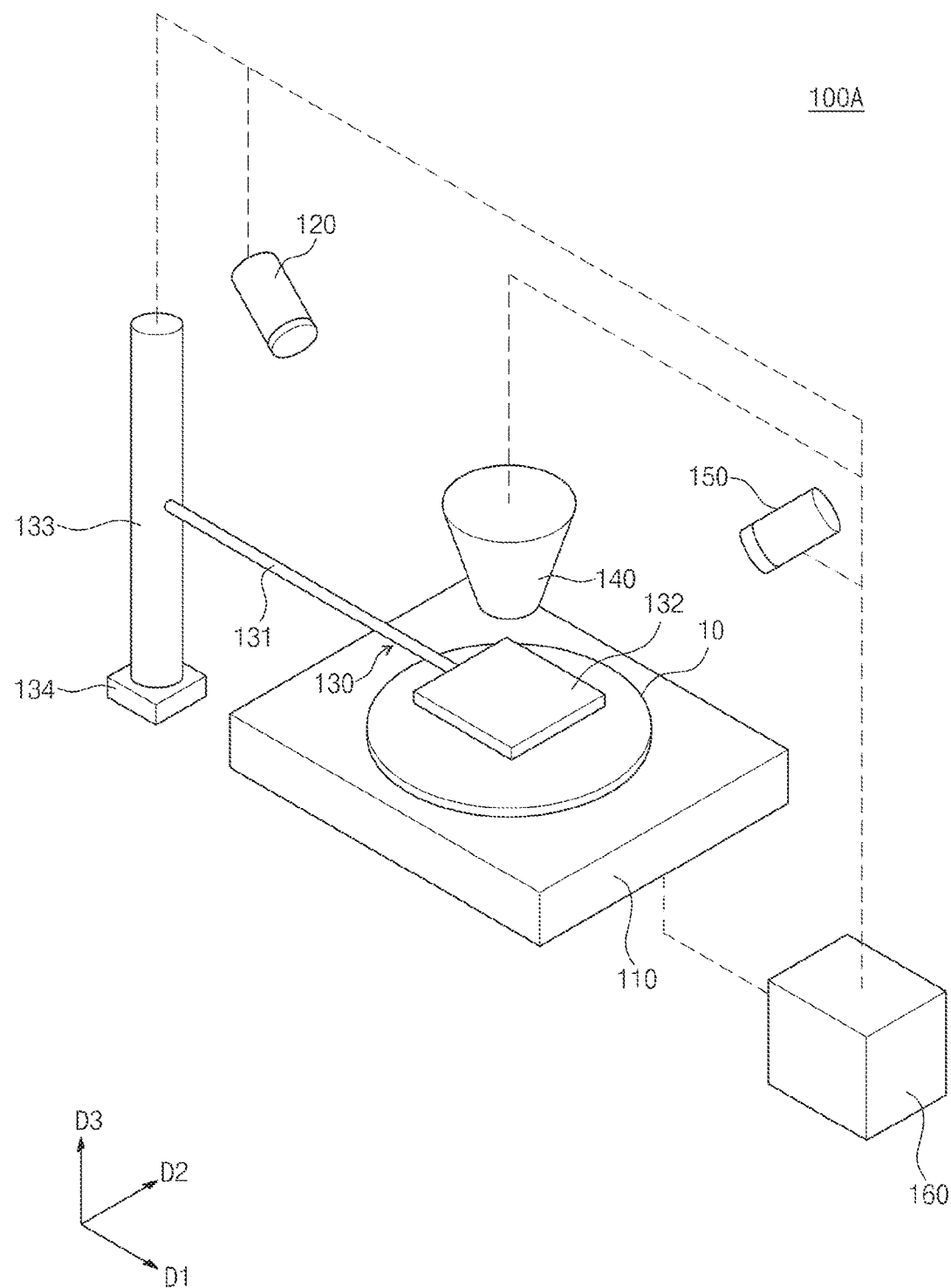
FIG. 2 is a perspective view schematically illustrating a substrate inspection apparatus according to some example embodiments of inventive concepts.
Figure 3A:
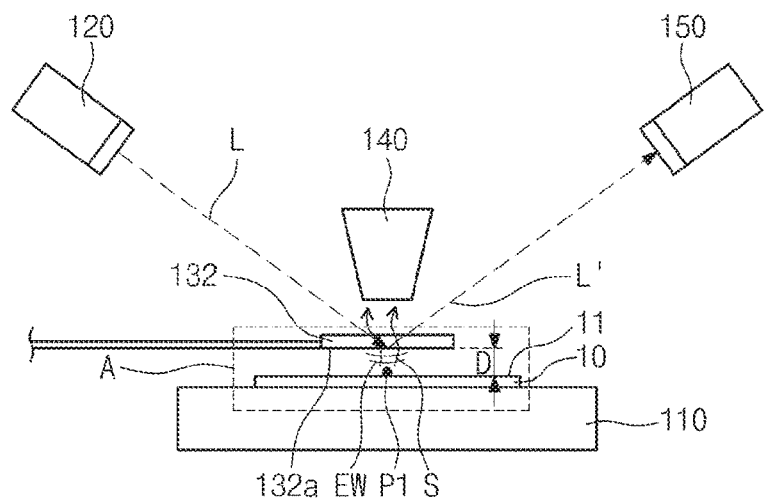
FIG. 3A is a side view of the substrate inspection apparatus of FIG. 2.

FIG. 2 is a perspective view schematically illustrating a substrate inspection apparatus according to some example embodiments of inventive concepts. FIG. 3A is a side view of the substrate inspection apparatus of FIG. 2, and FIG. 3B is an enlarged view of portion A of substrate inspection apparatus of FIG. 3A.

Figure 3B:
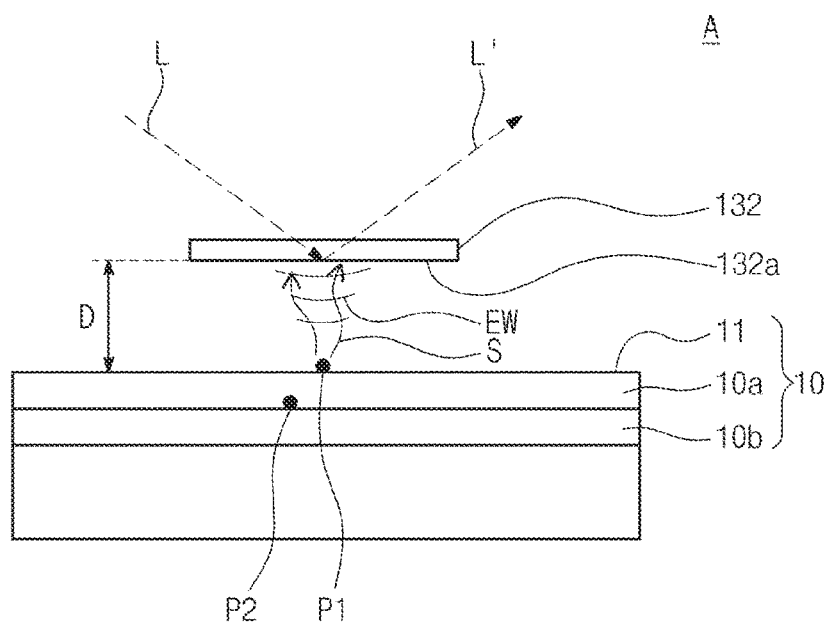
FIG. 3B is an enlarged view of portion A of the substrate inspection apparatus of FIG. 3A.

Referring to FIGS. 2, 3A, and 3B, a substrate inspection apparatus 100A may include at least a support 110, a light source 120, a light adjuster 130, a detector 140, a focus adjuster 150, and/or a controller 160.

The support 110 may be configured to support the substrate 10. The substrate 10 may include but not limiting to a wafer, for example. In some example embodiments, the substrate 10 may include but not limiting to a glass substrate, for example. The controller 160 may be configured to change position of the support 110 in at least first, second, and third directions, D2 and D3, respectively. The first, second, and third directions D1, D2 and D3 are orthogonal to each other. The first and second directions D1 and D2 may be selected to define an x-y plane, and the third direction D3 may be selected to be parallel to a z-axis. During the optical inspection process, the support 110 may be moved to perform a scanning operation on the substrate 10. Also, during the optical inspection process, the support 110 may be moved to allow the substrate 10 to be in focus.

The light source 120 may be disposed near the support 110. The light source 120 may be configured to emit an incident light L toward the substrate 10. That is, for example, the light source 120 may be configured to emit the incident light L toward a total reflector 132 of the light adjuster 130. The incident light L may be a laser beam. The light source 120 may be configured to change an incident angle and an incident position of the incident light L. Hereinafter, although some portion of the incident light L from the light source 120 may be absorbed by the total reflector 132, it may be ignored for clarity. In other words, it may be construed the incident light L from the light source 120 and the incident light L in the total reflector 132 have same intensity and energy, each other.

The light adjuster 130 may be disposed near the support 110. The light adjuster 130 may include the total reflector 132 positioned between the substrate 10 and the detector 140. The light adjuster 130 may be configured to allow the incident light L to be totally and/or substantially reflected.

Referring to FIGS. 3A and 3B, in particular, which illustrate an evanescent wave EW that may be produced as a result of the total reflection of the incident light L. The evanescent wave EW may be, for example, an electromagnetic wave (e.g., near-field light). The evanescent wave EW may have an intensity, which exponentially decreases with distance from its source. The total reflector 132 may be provided to be spaced apart from the top surface 11 of the substrate 10 by a critical distance D.

Under the aforementioned configuration of total reflector 132, optical characteristics of the evanescent wave EW may be dependent on the critical distance D. For example, the critical distance D may be defined as a distance at which the intensity of the evanescent wave EW decreases by a factor of 1/e. The critical distance D may vary depending on an incident angle, or wavelength of the incident light L, or a refractive index of any intervening medium. That is, for example, when the wavelength of the incident light L ranges from about 266 nm (nanometer) to about 355 nm, the critical distance D may be selected within a range from about 150 nm to about 300 nm. In general, the critical distance D may be given as follows (Equation 1):

$$D = \frac{\lambda(0)}{4\pi(n_1^2 \sin(\theta_i)^2 - n_2^2)^{1/2}}$$

where $\theta_i$ is an incident angle, $n_1$ and $n_2$ are refractive indices of first and second media, respectively, where $n_1 > n_2$ (e.g., $n_1$ is greater than $n_2$), and $\lambda 0$ is wavelength of an incident light in vacuum.

In an example embodiment where the incident light L is substantially totally reflected by a bottom surface 132a of the total reflector 132 to produce the evanescent wave EW, the evanescent wave EW may be allowed to reach the top surface 11 of the substrate 10, but not pass through the top surface 11. Thus, referring to FIG. 3B, where there is a first particle P1 on the top surface 11 of the substrate 10, the evanescent wave EW may optically interact with the first particle P1 to produce a scattering signal S. When the evanescent wave EW does not meet a near-field condition, the evanescent wave EW may have a vanishing intensity, and as such it is possible to limit and/or prevent the evanescent wave EW from passing through the top surface 11 of the substrate 10. The evanescent wave EW having a vanishing intensity may make it possible for the substrate inspection apparatus to limit and/or prevent an additional scattering signal from being produced by a second particle P2 on the lower layer 10b. Hereinafter, the desired defect on the substrate 10, such as the first particle P1, it may be referred as the defect P. Aforementioned, the defect P may be characterized as, for example, including but not limited to, contaminants (e.g., particles P1 shown in FIG. 3B) or abnormally-grown patterns may be categorized into a type of the defect.

Referring back to FIG. 2, the light adjuster 130 may include, in addition to the total reflector 132, at least a connection part 131, a supporting pillar 133, and a moveable base 134. The total reflector 132 may be, for example, a reflection prism for substantially totally reflecting the incident light L. The total reflector 132 may include denser material than the air.

Referring to FIGS. 2 and 3A, when the incident light L emitted from the light source 120 is incident on the total reflector 132, a total reflection may occur on the bottom surface 132a of the total reflector 132. The connection part 131, shown in FIG. 2, may be provided to connect the total reflector 132 to the supporting pillar 133. The supporting pillar 133 may include an end coupled to the moveable base 134. The moveable base 134 may be configured to change the position of the total reflector 132. That is, for example, the moveable base 134 may be configured to be able to move the total reflector 132 from an inspection position to a waiting position or vice versa.

In some example embodiments, the inspection position may be selected to allow the total reflector 132 to be located over an inspection region of the substrate 10. That is, for example, the inspection position may be selected to allow the total reflector 132 to be disposed between the substrate 10 and the detector 140. When the total reflector 132 is disposed over the inspection position, the total reflector 132 may overlap with the substrate 10 and the detector 140. In contrast, a waiting position may be selected to allow the total reflector 132 to be positioned out of the inspection position. In the waiting position, the total reflector 132 may be spaced apart from the substrate 10 in a horizontal direction, and may not overlap with the substrate 10 and the detector 140. The moveable base 134 may be configured to change a horizontal position of the total reflector 132 on the x-y plane. The moveable base 134 may also be configured to change a vertical position of the total reflector 132 in a direction along the z-axis.

Figure 5A:
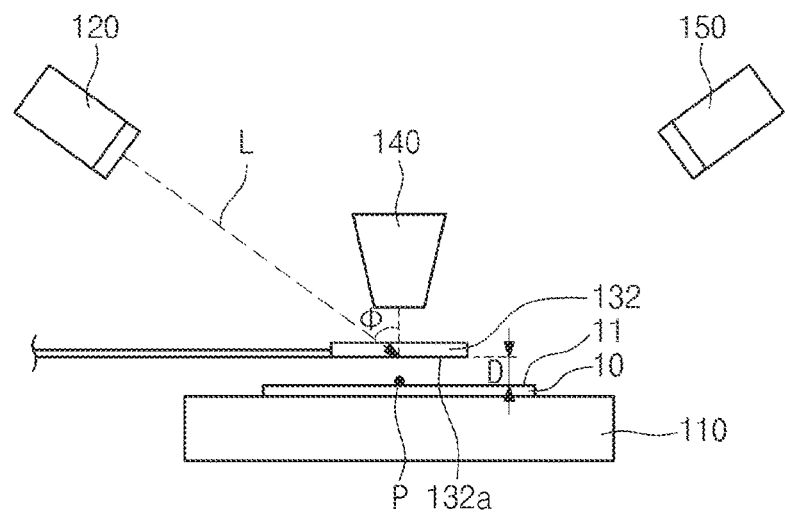
FIGS. 5A through 5C are diagrams illustrating the substrate inspection method of FIG. 4.
Figure 5B:
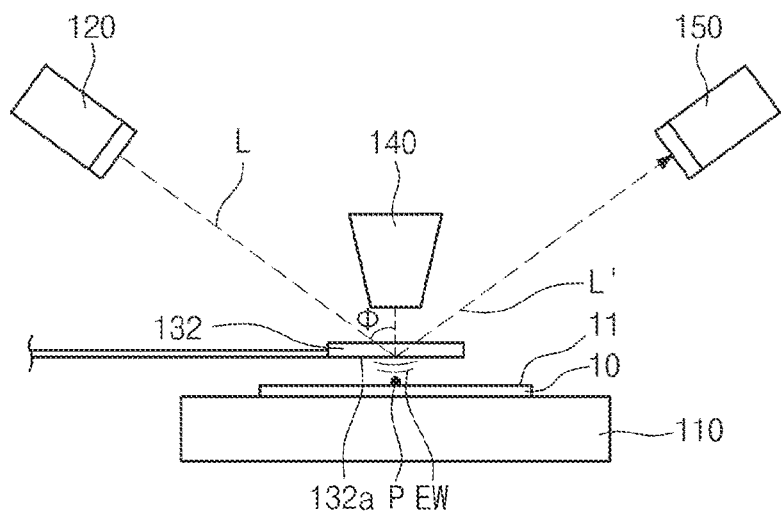
Figure 5C:
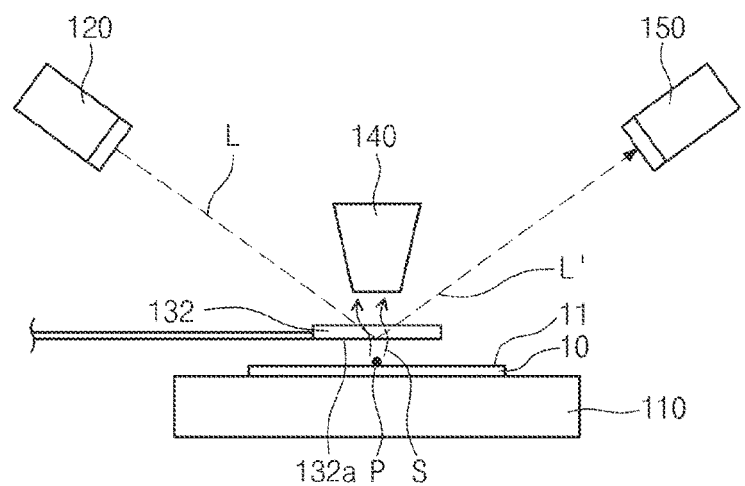

The detector 140 may be configured to detect the scattering signal S. The scattering signal S detected by the detector 140 may be transmitted to the controller 160. The scattering signal S produced by a defect P, for example, on the substrate 10, as illustrated in FIG. 5C, further discussed below, in order to reduce complexity in the drawings and to provide better understanding of inventive concepts. However, the scattering signal S may be generated from the entire region of the substrate 10, regardless of the presence or absence of the defect P.

Nevertheless, the presence of a defect P leads to a change in signal profile of the scattering signal S, and thus, the defect on the substrate 10 may be effectively detected by the detector 140. In some example embodiments, the detector 140 may be configured to obtain information on whether there is a defect P on the top surface 11 of the substrate 10. The information including but not limited to a size and a position of the defect P. As described above, the defect may be characterized as, for example, including but not limited to, contaminants (e.g., particles P1, P2) or abnormally-grown patterns.

Hereinafter, for the sake of simplicity, the description that follows will refer to an example in which a particle is the defect P, but inventive concepts may not be limited thereto. The detector 140 may be configured to detect the scattering signal S, which may be generated from the interaction between the evanescent wave EW and a defect on the top surface 11. The detector 140 may also be configured to digitize the scattering signal S. In some example embodiments, a plurality of detectors 140 may be provided in the substrate inspection apparatus 100A. As such, each of the plurality of detectors 140 may be spaced apart from the respective one of the plurality of detectors 140, and their arrangement may be variously changed. Each of the plurality of detectors 140 may include but not limited to at least one lens, a highly-sensitive CCD camera, or the like. In some example embodiments, each of the plurality of detectors 140 may further include a camera (not shown), and each of the plurality of detectors may be configured to directly measure patterns formed on the substrate 10.

The focus adjuster 150 may be disposed near the support 110. The focus adjuster 150 may be disposed to face the light source 120. The focus adjuster 150 may be configured to acquire focal information from a reflection light L' reflected from the substrate 10. The focal information acquired by the focus adjuster 150 may be transmitted to the controller 160, and may be used for a feedback operation.

Still referring to FIGS. 2, 3A and 3B the controller 160 may be configured to control the support 110, the light source 120, the light adjuster 130, the detector 140, and the focus adjuster 150. The controller may control the light source 120 to change an incident angle and an incident position of the incident light L. The controller 160 may analyze the scattering signal S transmitted from the detector 140. That is, for example, in the controller 160, the scattering signal S may be processed to produce a plurality of two-dimensional (2D) optical images (not shown) on the top surface 11 of the substrate 10. Furthermore, the images may be compared and analyzed to generate information on the presence or absence of the defect P. The generated information may include but not limited to size and position of the defect P. The scattering signal S generated from several regions of the substrate 10 may be compared or analyzed by the controller 160. If one of the scattering signals S that has been analyzed is founded to have a different property from the others, it may be classified as a defect P on the substrate 10.

The controller 160 may be further configured to perform an in-line monitoring on the substrate 10. In some example embodiments, the optical inspection process may be performed several times on the substrate 10. For example, under the control of the controller 160, a first inspection process may be performed, without the use of the light adjuster 130, and then, during a second inspection process the light adjuster 130 may be performed on the substrate 10. The controller 160 may include an image processing device (not shown) for processing the scattered signals and a library (not shown) for processing data obtained from the scattered signals. In other words, the controller 160, for example, may be configured to compare and analyze images, extract information on the presence or absence of a defect P, the information indicating for example a size of the defect P from the images, and display the information on a display monitor (not shown). In some example embodiments, the controller 160 may further include an additional analyzer (not shown). The additional analyzer may include, for example, including but not limited to a scanning electron microscope (SEM) or a transmission electron microscope (TEM) system.

Figure 4:
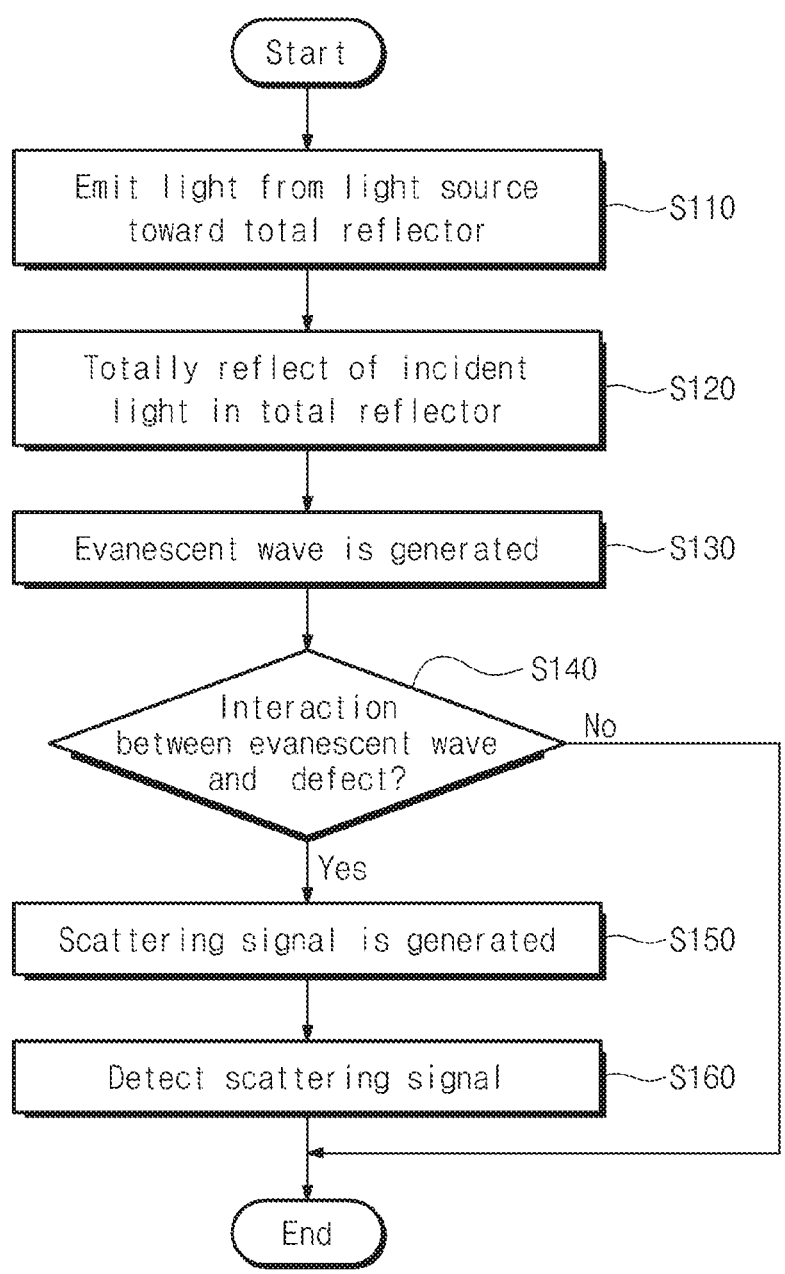
FIG. 4 is a flow chart illustrating an example of a substrate inspection method using the substrate inspection apparatus of FIG. 2.

FIG. 4 is a flow chart illustrating an example embodiment of a substrate inspection method using the substrate inspection apparatus of FIG. 2. FIGS. 5A through 5C are diagrams illustrating the substrate inspection method of FIG. 4. Hereinafter, a substrate inspection method according to some example embodiments of inventive concepts will be described with reference to FIGS. 4 and 5A through 5C.

Referring to FIG. 4 in conjunction with FIG. 5A, at S110, shown in FIG. 4, the total reflector 132 of the light adjuster 130 may be disposed at the inspection position, and then, the light source 120 may emit the incident light L towards the total reflector 132 of the light adjuster 130. At the inspection position, the total reflector 132 to be positioned between the substrate 10 and the detector 140. The total reflector 132 may be spaced apart from the top surface 11 of the substrate 10 by a critical distance D. The critical distance D, see Equation 1, may be selected within a range satisfying a near-field condition. For example, the critical distance D may be selected within a range from about 150 nm (nanometer) to about 300 nm. The incident light L may be controlled to have an incident angle of $\varphi$, as shown in FIGS. 5A and 5B. The incident angle $\varphi$, as shown in FIGS. 5A and 5B, may be selected to be greater than a critical angle ($\theta c$). When the incident angle $\varphi$ is greater than the critical angle ($\theta c$), the incident light L may be substantially totally reflected by the total reflector 132.

Referring to FIG. 4 in conjunction with FIG. 5B, at S120, shown in FIG. 4, the incident light L may be totally reflected by the bottom surface 132a of the total reflector 132. The substantially totally reflected light L' may have substantially the same or equal intensity as the reflection light L that is incident on the total reflector 132. At S130 when the incident light L is substantially totally reflected by the bottom surface 132a of the total reflector 132, the evanescent wave EW may be generated. Where the total reflector 132 is spaced apart from the substrate 10 by the critical distance D, the evanescent wave EW may be allowed to reach the top surface 11 of the substrate 10.

Referring to FIG. 4 in conjunction with FIG. 5C, at S140, shown in FIG. 4, it is determined whether there is an interaction between the defect P on the top surface 11 of the substrate 10 and the evanescent wave EW. At S150 a scattering signal S is generated if it is determined that there is an interaction between the defect P and the evanescent wave EW. At S160 the scattering signal S may pass through the total reflector 132, and the scattering signal S may be incident into the detector 140.

The scattering signal S may be transmitted from the detector 140 to the controller 160. In the controller 160, the scattering signal S may be processed to extract information on whether there is a defect P on the top surface 11 of the substrate 10, such as determining size of the defect P. Since the presence of the defect P affects the scattering signal S, a difference between multiple scattering signals S may be used in the controller 160 to obtain the information on the defect P. Where the total reflector 132 is spaced apart from the substrate 10 by the critical distance D or a near-field distance, the evanescent wave EW may not pass through the top surface 11 of the substrate 10. As such, this may make it possible to limit and/or prevent an additional scattering signal S from being produced by underlying elements (e.g., a layer below the top surface 11 or the support 110), and thereby reducing noise in the scattering signals S.

Figure 6:
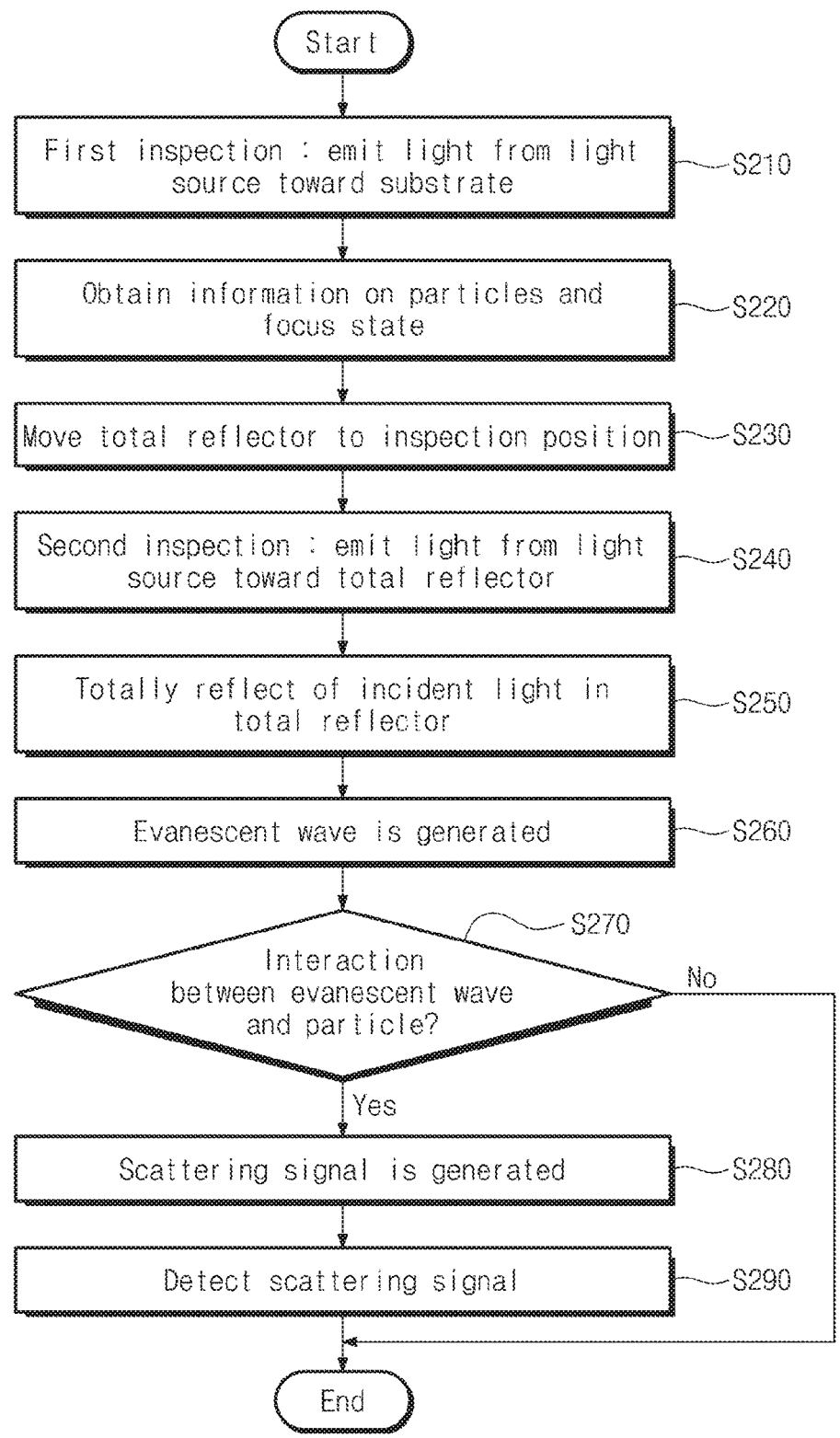
FIG. 6 is a flow chart illustrating an example of a substrate inspection method using the substrate inspection apparatus of FIG. 2.

FIG. 6 is a flow chart illustrating an example embodiment of a substrate inspection method using the substrate inspection apparatus of FIG. 2. FIGS. 7A through 7F are diagrams illustrating the substrate inspection method of FIG. 6. Hereinafter, a substrate inspection method according to some example embodiments of inventive concepts will be described with reference to FIGS. 6 through 7F.

Figure 7A:
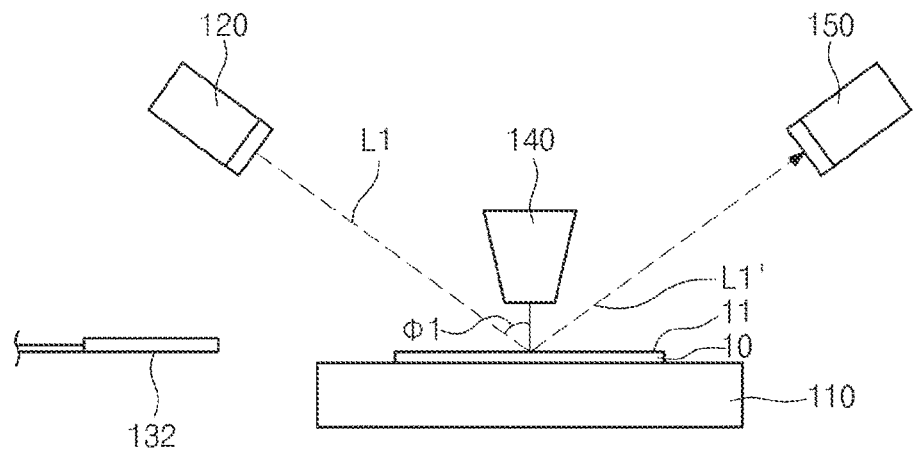
FIGS. 7A through 7F are diagrams illustrating the substrate inspection method of FIG. 6.

Referring to FIG. 6 in conjunction with FIG. 7A, the controller 160 may control the light source 120 and the light adjuster 130 to perform a first inspection process. Under the control of the controller 160, the total reflector 132 may be disposed in the waiting position. The waiting position may be selected to allow the total reflector 132 to be spaced apart from the substrate 10.

At S220, shown in FIG. 6, the controller 160 may control the light source 120 to allow a first incident light L1 to be emitted towards the top surface 11 of the substrate 10 during the first inspection process. The first incident light L1 may be incident on the top surface 11 of the substrate 10 at a first incident angle φ1. The first incident angle φ1 may be changed, and the detector 140 may collect a scattering signal (not shown), which may be generated when the first incident light L1 is incident on the substrate 10. The scattering signal (not shown) collected by the detector 140 may be transmitted to the controller 160. The focus adjuster 150 may receive the first reflection light L1' and may obtain focal information from the first reflection light L1'. The focus adjuster 150 may transmit the obtained focal information to the controller 160 for purposes of feedback operation.

Figure 7B:
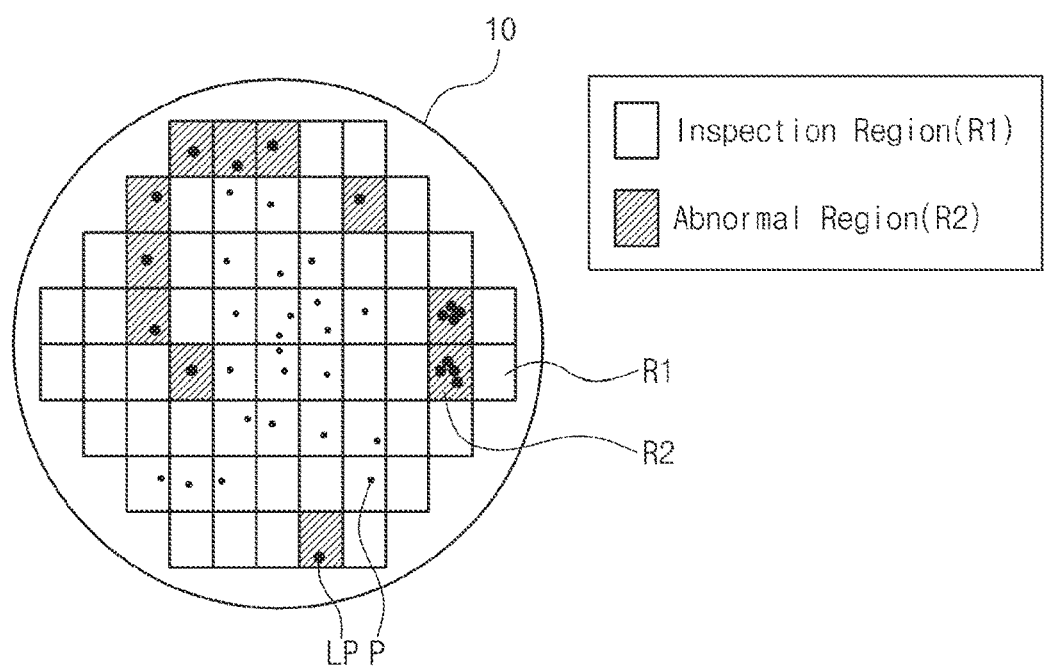

Referring to FIG. 6 in conjunction with FIG. 7B, as a result of the first inspection process, at S220, shown in FIG. 6, the controller 160 may obtain information on particles P and LP formed on the top surface 11 of the substrate 10. For example, since the presence of a defect P affects the scattering signals S, a difference between the scattering signals S may be used by the controller 160 to obtain information on the presence or absence of the defect. The substrate 10 may include a plurality of regions. Based on the information of the defect P, the controller 160 may classify the plurality of regions into two types, for example, abnormal regions R2 and inspection regions R1. That is, for example, when a particle LP is produced on at least one of the plurality of regions having a larger size than a desired (and/or alternatively predetermined) size, then the at least one the plurality of regions may be classified as the abnormal region R2. Or else, the at least one of the plurality of regions may be classified as the inspection region R1. Here, the desired (and/or alternatively predetermined) size may be substantially equal to or substantially larger than the critical distance D. In addition, at S220 the controller 160 may obtain the focal information obtained in the first inspection process.

Figure 7C:
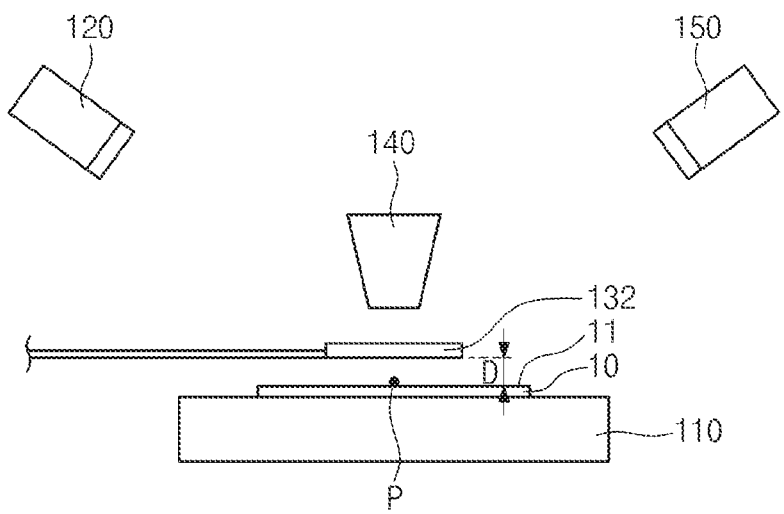

Referring to FIG. 6 in conjunction with FIG. 7C, at S230, shown in FIG. 6, under the control of the controller 160, at S230, the total reflector 132 may be positioned in the inspection position. The inspection position may be selected to allow the total reflector 132 to be positioned between the substrate 10 and the detector 140. When the total reflector 132 is positioned in the inspection position, the total reflector 132 may be spaced apart from the top surface 11 of the substrate 10 by the critical distance D. The critical distance D may be selected within a range satisfying the near-field condition. That is, for example, the critical distance D may be selected within a range from about 150 nm (nanometer) to about 300 nm. The second inspection process may be performed on the inspection region R1, and not on the abnormal region R2. This may make it possible to limit and/or prevent the total reflector 132 from colliding with the large particle LP in its path and thereby limit and/or prevent additional defects from being produced on the substrate 10. In the second inspection process, focal positions of the total reflector 132 and the substrate 10 may be controlled by the controller 160.

Figure 7D:
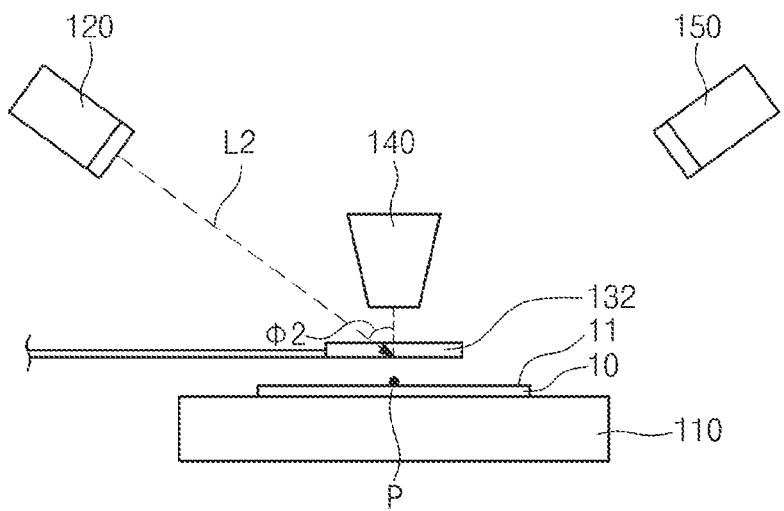

Referring to FIG. 6 in conjunction with FIG. 7D, at S240, shown in FIG. 6, the controller 160 may control the light source 120 to allow a second incident light L2 to be incident on the total reflector 132 in order to perform a second inspection on the substrate 10. The second incident light L2 may be incident on the total reflector 132 at a second incident angle φ2. The second incident angle φ2 may be selected to be greater than a critical angle (θc). When the second incident angle φ2 is greater than the critical angle (θc), the second incident light L2 may be substantially totally reflected by the total reflector 132.

Figure 7E:
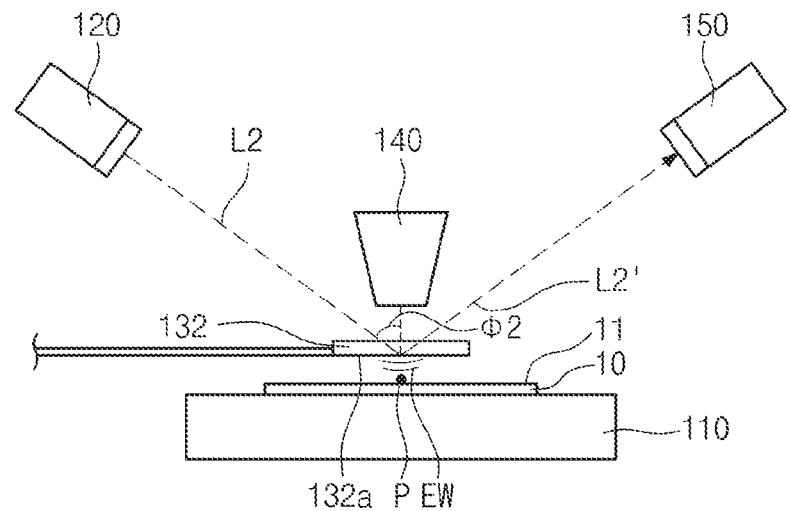

Referring to FIG. 6 in conjunction with FIG. 7E, at S250, shown in FIG. 6, the second incident light L2 may be substantially totally reflected by the bottom surface 132a of the total reflector 132. The substantially totally reflected fraction L2' may have substantially the same intensity as the second incident light L2, which is incident on the total reflector 132.

At S260, when the second incident light L2 is substantially totally reflected by the bottom surface 132a of the total reflector 132, the evanescent wave EW may be generated. Where the total reflector 132 is spaced apart from the substrate 10 by the critical distance D and/or at a near-field distance, the evanescent wave EW may be allowed to reach the top surface 11 of the substrate 10.

Figure 7F:
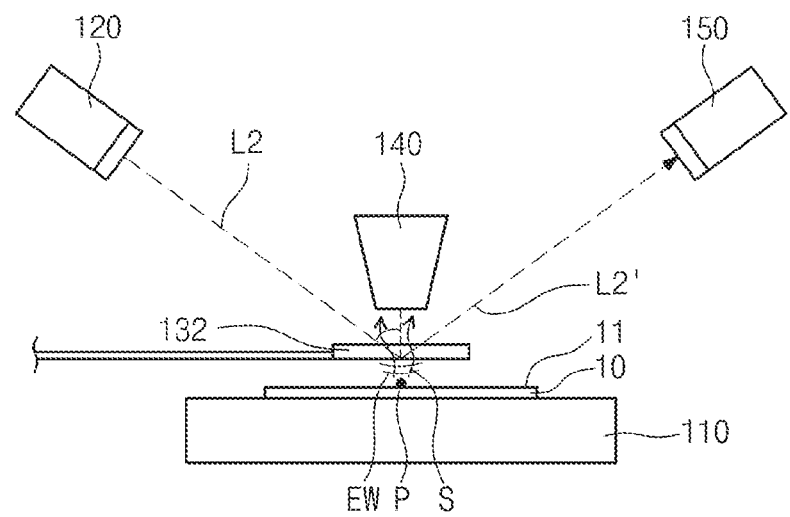

Referring to FIG. 6 in conjunction with FIG. 7F, at S270, shown in FIG. 6, it is determined whether there is interaction between a particle P on the top surface 11 of the substrate 10 and the evanescent wave EW. At S280, a scattering signal S may be generated if it is determined that there is an interaction between the evanescent wave EW and the particle P. At S290, the scattering signal S may thereafter pass through the total reflector 132 and may be incident into the detector 140. Thereafter, the scattering signal S may be transmitted from the detector 140 to the controller 160. Since the presence of a defect affects the scattering signal S, a difference between the scattering signal S in the controller 160 may be used to obtain the information on the defect. Where the total reflector 132 is spaced apart from the substrate 10 by the critical distance D, and/or at the near-field distance, it is possible to substantially limit and/or prevent the evanescent wave EW from propagating into the substrate 10 through the top surface 11. This may make it possible to limit and/or prevent an additional scattering signal from being produced by underlying elements (e.g., a layer below the top surface 11 or the support 110), and thereby reducing noise in the scattering signals S.

Figure 8:
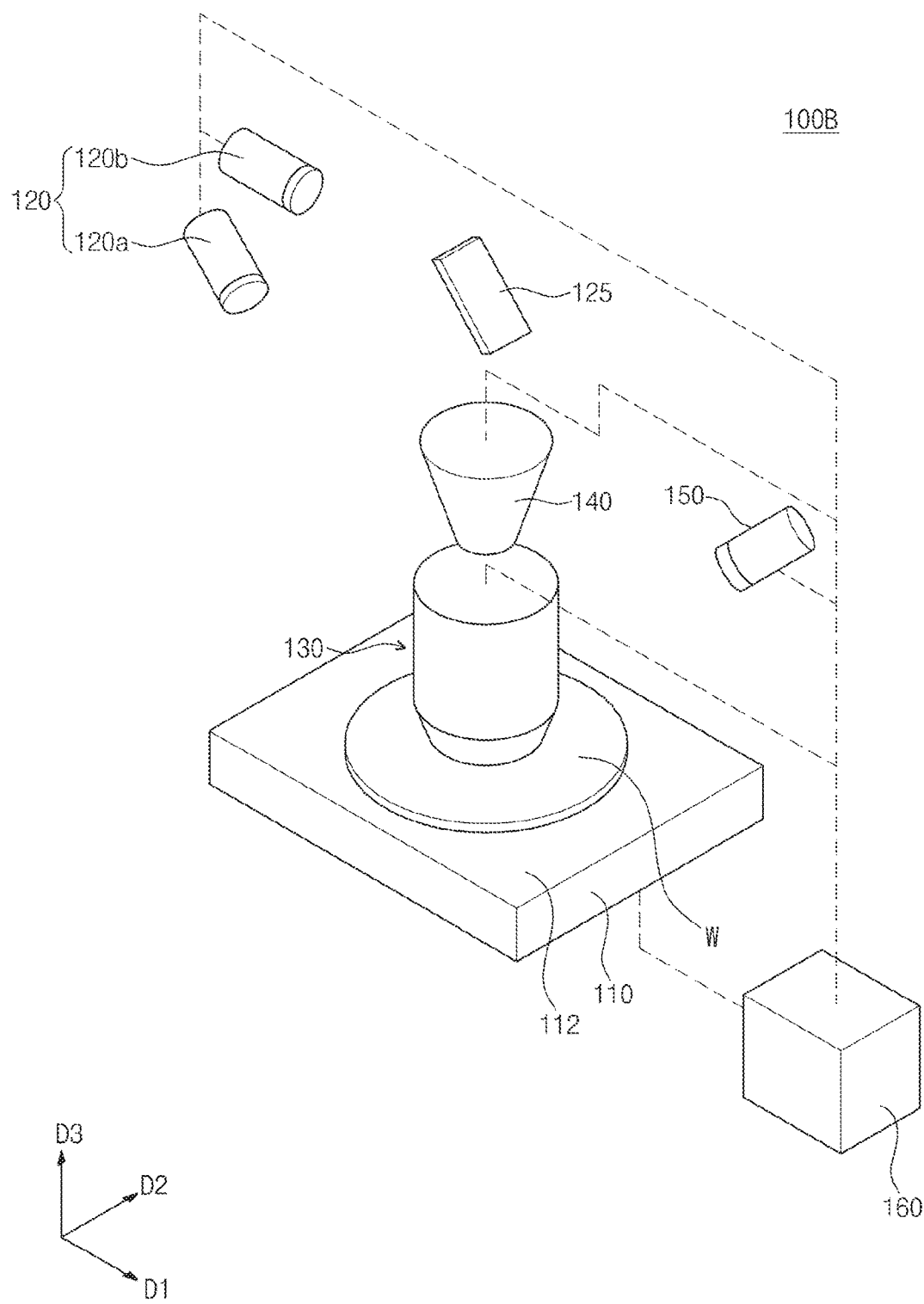
FIG. 8 is a perspective view schematically illustrating a substrate inspection apparatus according to some example embodiments of inventive concepts.
Figure 9:
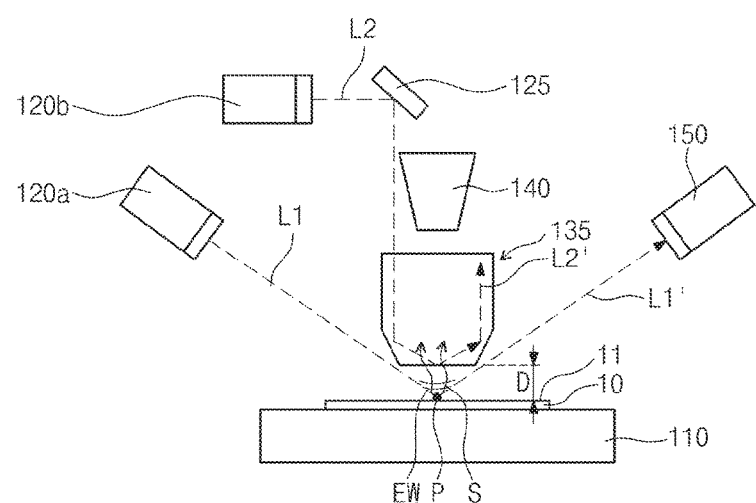
FIG. 9 is a side view of the substrate inspection apparatus of FIG. 8.
Figure 10A:
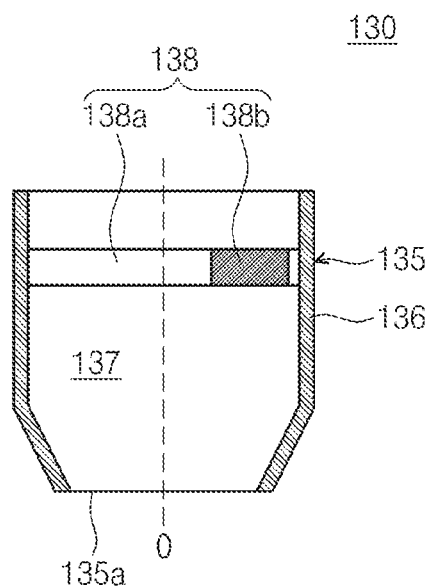
FIG. 10A is a sectional view illustrating an example embodiment of a light-condenser of FIGS. 8 and 9.
Figure 10B:
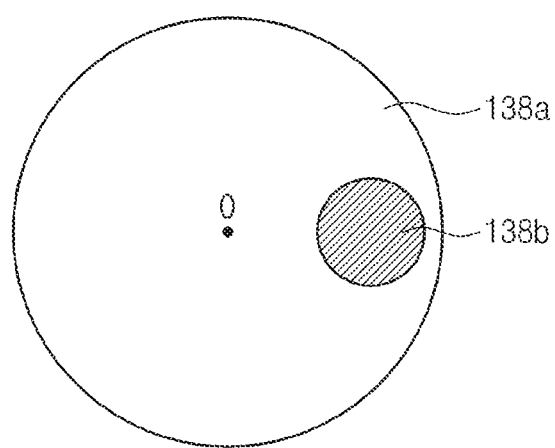
FIG. 10B is a plan view illustrating an example embodiment of a filter of FIGS. 8 and 9.

FIG. 8 is a perspective view schematically illustrating a substrate inspection apparatus according to some example embodiments of inventive concepts. FIG. 9 is a side view of FIG. 8. FIG. 10A is a sectional view illustrating a light-condenser of FIGS. 8 and 9, and FIG. 10B is a plan view illustrating a filter of FIGS. 8 and 9.

Referring to FIGS. 8 through 10B, a substrate inspection apparatus 100B may include at least a support 110, a light source 120, a light adjuster 130, a detector 140, a focus adjuster 150, and a controller 160. In the following description of the substrate inspection apparatus 100B, substantially the same element as any of the substrate inspection apparatus 100A previously described with reference to FIGS. 2 through 3B may be identified by a similar and/or identical reference(s) number, without repeating an overlapping description thereof.

The substrate inspection apparatus 100B may include a plurality of light sources 120. The plurality of light sources 120 may include a first light source 120a and a second light source 120b. The first light source 120a may be configured to directly emit a first incident light L1 onto the substrate 10, and the second light source 120b may be configured to directly and/or indirectly emit the second incident light L2 onto the light adjuster 130.

FIGS. 8 and 9 illustrate the substrate inspection apparatus 100B, in which two light sources 120a and 120b are provided, but in some embodiments, the light sources 120 may be provided in the form of a single light source, whose incident position and angle can be changed. That is, for example, the substrate inspection apparatus 100B of FIG. 8 may include only the second light source 120b, which may be configured to directly and/or indirectly emit the second incident light L2 onto the light adjuster 130. An optical member 125 may be disposed along a propagation path of the second incident light L2 from the second light source 120b to the light adjuster 130. The optical member 125 may include but is not limited to, a mirror.

Referring to FIG. 10A, the light adjuster 130 may include at least a light-condenser 135 and a filter 138. The light-condenser 135 may be provided over the inspection region of the substrate 10. The light-condenser 135 may be including but not limited to an objective lens. The light-condenser 135 may further include a housing 136. The housing 136 may include an internal space 137, in which a total and/or substantially reflection of the second incident light L2 occurs (e.g., see FIG. 12C, discussed below in detail). The light-condenser 135 may further include a bottom surface 135a. The bottom surface 135a of the light-condenser 135 may be configured to allow light incident thereon to be totally and/or substantially reflected. In some example embodiments, a lens may be positioned in the light-condenser 135, and as such the bottom surface 135a of the light-condenser 135 may be used at least as a surface of lens. Alternatively, a reflection prism may be positioned in the light-condenser 135, and as such the bottom surface 135a of the light-condenser 135 may be used at least as a surface of the reflection prism.

Still referring to FIG. 10A, the filter 138 may be provided in the light-condenser 135. The filter 138 may be configured to limit and/or prevent the substantially totally reflected fraction L2' of the second reflection light L2 from passing there through (e.g., see FIG. 12D, discussed below in detail). For example, the substantially totally reflected fraction L2' of the second reflection light L2 may be absorbed or reflected by the filter part 138b of the filter 138, and thus, it is possible to prevent the scattering signal S from being interfered and disturbed by the substantially totally reflected fraction L2' of the second reflection light L2. The filter 138 may include a transmissive part 138a and a filter part 138b. The filter part 138b may be provided to have its center spaced apart from a center axis O of the internal space 137. The transmissive part 138a may be provided to enclose the filter part 138b.

As shown in FIG. 10B, the transmissive part 138a may be provided such that its center is positioned on substantially the center axis O of the internal space 137, and the filter part 138b may be provided in such a way that it passes through the transmissive part 138a at a position spaced apart from the center axis O. The transmissive part 138a may be formed of a transparent material such as including but not limited to glass. The transmissive part 138a and the light-condenser 135 may be configured to allow the second incident light L2 to be substantially totally reflected in the internal space 137. The filter part 138b may be configured to limit and/or prevent light with a specific wavelength from passing there through.

Referring back to FIG. 9, an evanescent wave EW may be generated as a result of the reflection of the second incident light L2 in the internal space 137. The evanescent wave EW may be including but not limited to near-field light. The evanescent wave EW may have an intensity exponentially decreasing with distance from its source. The light-condenser 135 may be provided to be spaced apart from the top surface 11 of the substrate 10 by a critical distance D. The critical distance D may be selected within a range satisfying the near-field condition. That is, for example, the critical distance D may be selected within a range from about 150 nm (nanometer) to about 300 nm. In some example embodiments, the evanescent wave EW may be allowed to reach the top surface 11 of the substrate 10. Accordingly, where there is a defect P on the top surface 11 of the substrate 10, the evanescent wave EW may optically interact with the defect P to produce a scattering signal S. The detector 140 may be configured to detect the scattering signal S transmitted through the transmissive part 138a included in the light-condenser 135. Since the light-condenser 135 includes the transmissive part 138a and the filter part 138b, it is possible for the detector 140 to distinguish the scattering signal S from the second reflection light L2', which is substantially totally reflected in the light-condenser 135. The light-condenser 135 may further include optical components such as including but not limited to a mirror.

Figure 11:
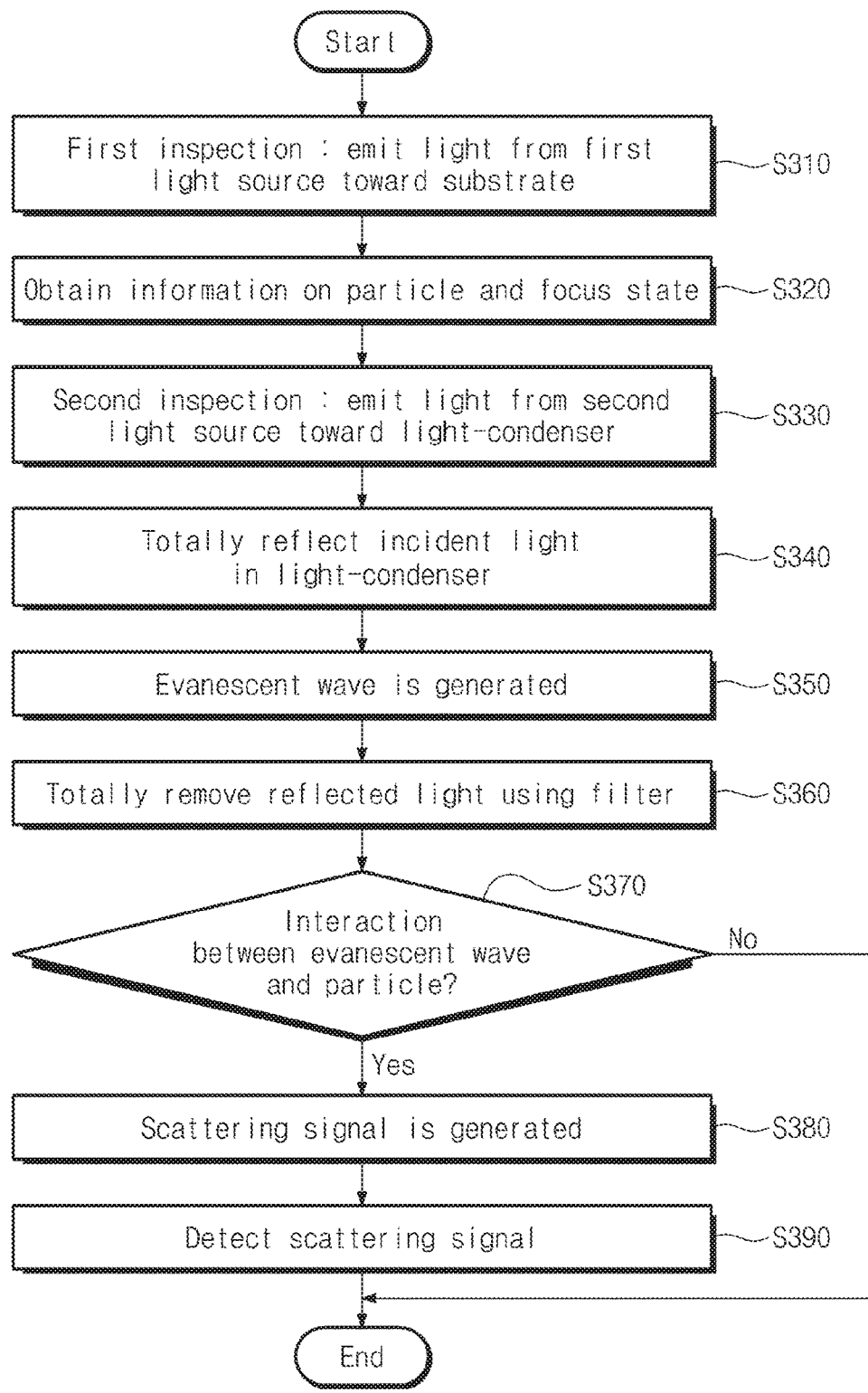
FIG. 11 is a flow chart illustrating an example of a substrate inspection method using the substrate inspection apparatus of FIG. 8.

FIG. 11 is a flow chart illustrating an example embodiment of a substrate inspection method using the substrate inspection apparatus of FIG. 8. FIGS. 12A through 12D are diagrams illustrating the substrate inspection method of FIG. 11. Hereinafter, a substrate inspection method according to some example embodiments of inventive concepts will be described with reference to FIGS. 11 through 12D. For concise description, a previously described element and/or feature may be identified by a similar and/or identical reference number(s) without repeating an overlapping description thereof.

Figure 12A:
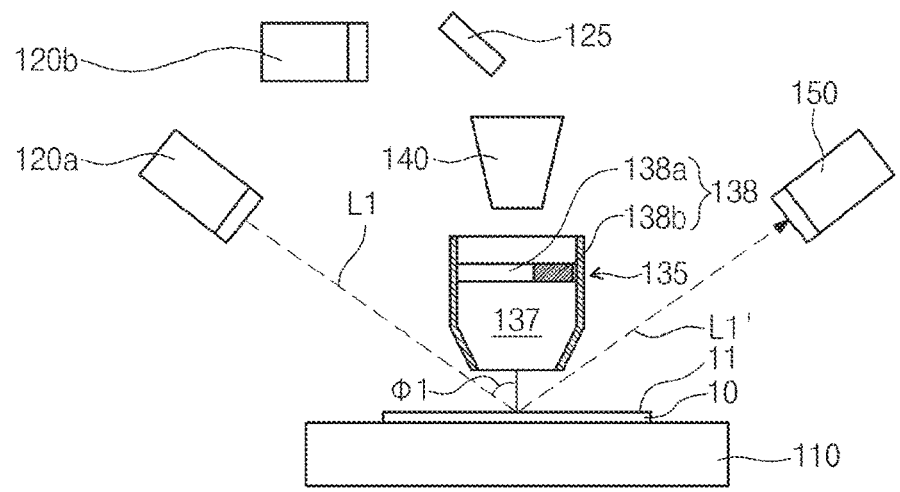
FIGS. 12A through 12D are diagrams illustrating the substrate inspection method of FIG. 11.

Referring to FIGS. 11 and 12A, the controller 160 may perform a first inspection process by controlling the light sources 120 and the light-condenser 135 included in the light adjuster 130. At S310, shown in FIG. 11, during the first inspection process, the controller 160 may control the first light source 120a to allow the first incident light L1 to propagate toward the top surface 11 of the substrate 10. The first incident light L1 may be incident on the top surface 11 of the substrate 10 at a first incident angle φ1. Here, the first incident angle φ1 may be changed, and thus, an intensity of the first reflection light L1' may be lower than the first incident light L1 incident on the substrate 10. The detector 140 may collect a scattering signal (not shown in FIG. 12A), which may be generated when the first incident light L1 is incident on the substrate 10. The scattering signal (not shown in FIG. 12A) collected by the detector 140 may be transmitted to the controller 160. The focus adjuster 150 may obtain focal information from the first reflection light L1'.

Still referring to FIG. 11, at S320, as a result of the first inspection process, the controller 160 may obtain information on particles existing on the top surface 11 of the substrate 10. The substrate 10 may include a plurality of regions. Similar to example embodiment of FIG. 7B, the controller 160 may classify each of the plurality of regions into two types: abnormal regions R2 and inspection regions R1. The controller 160 classifies each of the plurality of regions based on the information on the defect received by the controller 160. That is, for example, when a particle LP is produced on at least one of the plurality of regions to have a larger size than a desired (and/or alternatively predetermined) size, such a region may be classified as the abnormal region R2. Otherwise the region may be classified as the inspection region R1. Additionally, at S320, the controller 160 may obtain the focal information obtained in the first inspection process.

Figure 12B:
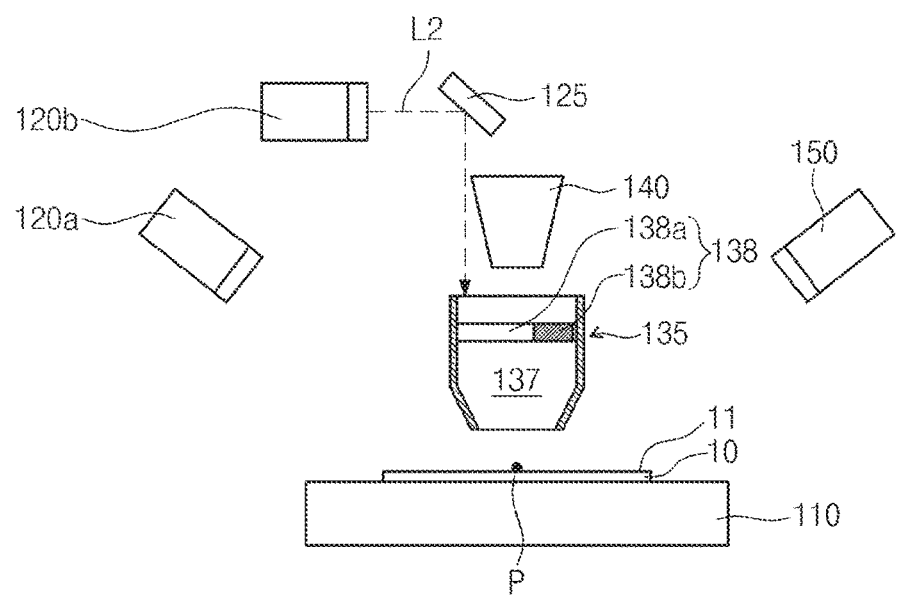

Referring to FIG. 11 in conjunction with FIG. 12B, at S330, shown in FIG. 11, during the second inspection process, the controller 160 may control the light sources 120 and the light-condenser 135. At S330, the controller 160 may control the second light source 120*b* to allow the second incident light L2 to propagate toward the light-condenser 135. The second incident light L2 may be incident into the internal space 137 of the light-condenser 135. The propagation path of the second incident light L2 may be controlled to pass through a portion of the transmissive part 138*a* that is spaced apart from a center of the light-condenser 135. Under the control of the controller 160, the second inspection process may be performed on other regions, other than a region provided with a large defect. This may make it possible to limit and/or prevent the light-condenser 135 from colliding with the large particle LP in its path and thereby to limit and/or prevent additional defects from being produced on the substrate 10. In the second inspection process, the focal positions of the light-condenser 135 and the substrate 10 may be controlled by the controller 160.

Figure 12C:
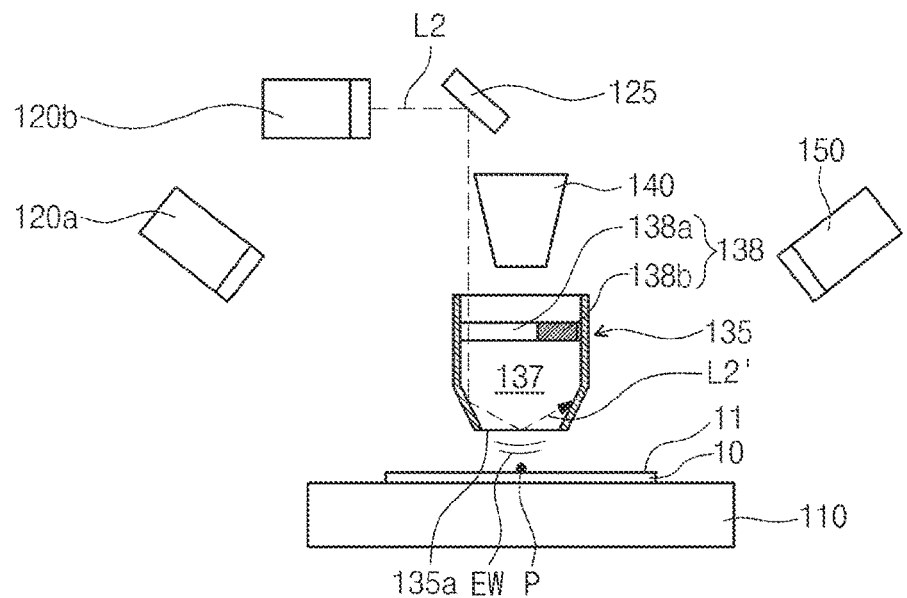

Referring to FIG. 11 in conjunction with FIG. 12C, at S340, shown in FIG. 11, the second incident light L2 may be totally and/or substantially reflected in the internal space 137 of the light-condenser 135. The substantially totally reflected fraction L2' may have substantially the same intensity as the second incident light L2 that is incident on the total reflector 132. At S350, shown in FIG. 11, when the second incident light L2 is substantially totally reflected by the internal space 137, the evanescent wave EW may be generated. Where the light-condenser 135 is spaced apart from the substrate 10 by the critical distance D and/or at a near-field distance, the evanescent wave EW may be allowed to reach the top surface 11 of the substrate 10.

At S360, shown in FIG. 11, the substantially totally reflected fraction L2' of the second incident light L2 may be absorbed and/or reflected by the filter part 138*b* in the filter 138. As such, it is possible to limit and/or prevent the scattering signal S from being interfered and disturbed by the substantially totally reflected fraction L2' of the second incident light L2.

Figure 12D:
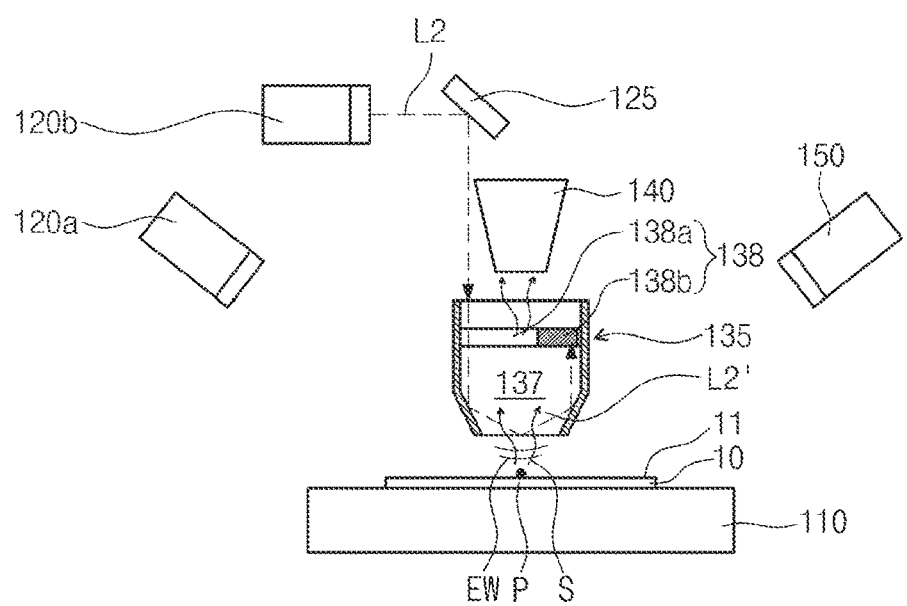

Referring to FIGS. 11 and 12D, at S370, shown in FIG. 11 it is determined whether the particle P on the top surface 11 of the substrate 10 and the evanescent wave EW may have optically interacted with each other. At S380, a scattering signal S may be generated if the particle P and the evanescent wave EW have interacted with each other. At S390, the scattering signal S may pass through the light-condenser 135 and may be incident into the detector 140. Thereafter, the scattering signal S may be transmitted from the detector 140 to the controller 160. Since the presence of the defect affects a plurality of scattering signals S, a difference between each of the scattering signals S may be used by the controller 160 to obtain the information on the defect.

In the case where the light-condenser 135 is spaced apart from the substrate 10 by the critical distance D of the near-field distance, it is possible to substantially limit and/or prevent the evanescent wave EW from propagating into the substrate 10 through the top surface 11. This may make it possible to limit and/or prevent an additional scattering signal from being produced by underlying elements (e.g., a layer below the top surface 11 or the support 110) and thereby reducing noise in the plurality of scattering signals S.

As described with reference to FIGS. 11 and 12A to 12D, an optical inspection process may be performed several times with the substrate inspection apparatus 100B of FIG. 8. However, in some example embodiments, it is obvious to one of ordinary skill in the art to perform an optical inspection process once using the substrate inspection apparatus 100B of FIG. 8, as described with reference to FIGS. 4 and 5A to 5C.

The above description has referred to the substrate inspection apparatuses 100A and 100B including the total reflector 132 or the light-condenser 135, which are configured to realize total reflection of an incident light; however, inventive concepts are not limited thereto. For example, various optical members capable of providing total reflection of an incident light may be used in the substrate inspection apparatus according to some example embodiments of inventive concepts. As an example, the substrate inspection apparatuses 100A and 100B may be configured to perform the optical inspection process using at least a total reflection mirror. In addition, some optical components may be additionally included in the substrate inspection apparatuses 100A and 100B to improve efficiency in the optical inspection process. That is, for example, the substrate inspection apparatuses 100A and 100B may be configured to further include at least one mirror and/or at least one light-condenser 135.

Furthermore, for the sake of brevity, the above description has referred to the substrate inspection apparatuses 100A and 100B including the light source 120, which is configured to emit single light beam, the light source 120 may be provided in the form of a surface light source. In order to reduce complexity in the drawings, the particle P is illustrated as if it is a sole origin required for generating the scattering signal S from the top surface 11 of the substrate 10; however, the scattering signal S may be generated from the entire region of the substrate 10, independent of the presence and/or absence of the defect. The above description has referred to the substrate inspection apparatuses 100A and 100B, which are configured to measure a defect on the substrate 10 based on the scattering signal S; however in some example embodiments the substrate inspection apparatus may be configured to include an additional camera (not shown) for measuring patterns formed on the substrate 10.

The above description has referred to the substrate inspection apparatuses 100A and 100B including the light source 120, which is configured to emit the incident light directly toward the substrate 10 and/or the light adjuster 130. However, the substrate inspection apparatuses 100A and 100B may further include at least one optical component, which is provided between the light source 120 and the substrate 10 and/or the light adjuster 130, in order to increase a surface area covered by the incident light. That is, for example, by increasing the number of laser beams or an area of the laser beam, it is possible to increase the surface area covered by the incident light. As a non-limiting example, by adding a travelling lens on the propagation path of the incident light, it is possible to increase the number of the laser beams. Additionally, by adding a cylindrical lens on the propagation path of the incident light, it is possible to increase the area of the laser beam. The increase in surface area covered by the incident light may make it possible to reduce process time taken for the optical inspection process.

According to some example embodiments of inventive concepts, an evanescent wave EW, which is generated when light is substantially totally reflected, may be used to obtain a scattering signal S containing information on a defect on a substrate 10. That is, for example, a light adjuster 130, which allows the light to be substantially totally reflected, is provided to be spaced apart from a top surface 11 of the substrate 10 within a distance range D satisfying a near-field condition. As such, making it possible to allow the evanescent wave EW to reach the top surface 11 of the substrate 10.

Accordingly, in example embodiment where there is a defect on the top surface 11 of the substrate 10, the evanescent wave EW may optically interact with the defect to generate the scattering signal S. A detector 140 may extract information on the defect from the scattering signal S. Since an intensity of the evanescent wave EW decreases exponentially with distance from a wave source, it is possible to limit and/or prevent the scattering signal S from being disturbed by underlying elements positioned below the top surface 11 of the substrate 10. That is, for example, it is possible to reduce noise and improve efficiency and reliability in a substrate inspection process 100A and 100B as shown in FIGS. 2 and 8. It should be understood that example embodiments described herein should be considered in a descriptive sense only and not for purposes of limitation. Descriptions of features or aspects within each device or method according to example embodiments should typically be considered as available for other similar features or aspects in other devices or methods according to example embodiments. While some example embodiments of inventive concepts have been particularly shown and described, it will be understood by one of ordinary skill in the art that variations in form and detail may be made therein without departing from the spirit and scope of the attached claims.

What is claimed is:

1. A substrate inspection apparatus comprising:
a light source configured to emit an incident light;
a support configured to support a substrate;
a detector configured to detect a defect on the substrate based on a generated scattering signal received by the detector; and
a light adjuster configured to substantially totally reflect the incident light, the generated scattering signal is generated based on an optical interaction between an evanescent wave and the defect on the substrate, the evanescent wave is generated when the incident light is reflected by the light adjuster,
wherein the light adjuster comprises a reflection prism; and a moveable base configured to change a position of the reflection prism,
wherein the moveable base is configured to move the reflection prism from an inspection position to a waiting position, the inspection position is when the reflection prism is between the substrate and the detector, the waiting position is when the reflection prism is not between the substrate and the detector.

2. The substrate inspection apparatus of claim 1, wherein the light adjuster is between the detector and the substrate.

3. The substrate inspection apparatus of claim 2, wherein the light adjuster and a top surface of the substrate are separated from each other by a distance, and the evanescent wave is configured to reach the top surface but not pass through the top surface.

4. The substrate inspection apparatus of claim 3, wherein a range of the distance is from 150 nm (nanometer) to 300 nm.

5. The substrate inspection apparatus of claim 1, further comprising:
a controller configured to,
extract information on the defect from the generated scattering signal, and
control the light adjuster to perform a first inspection process and a second inspection process, the first inspection process includes the reflection prism at the waiting position, and the second inspection process includes the reflection prism at the inspection position.

6. The substrate inspection apparatus of claim 5, wherein the controller is further configured to,
determine whether there is a first region within the defect during the first inspection process, the first region is an abnormal region which includes a size larger than a desired size, and
perform the second inspection process on a second region of the substrate, the second region is different from the abnormal region.

7. The substrate inspection apparatus of claim 1, wherein the light adjuster comprises:
a light-condenser configured to reflect the incident light within the light-condenser; and
a filter configured to remove a reflected fraction of the incident light.

8. The substrate inspection apparatus of claim 7, wherein the filter comprises:
a transmissive part configured to have the incident light incident into an inner space of the light adjuster; and
a filter part configured to limit propagation of the reflected fraction from the inner space to the light adjuster.

9. The substrate inspection apparatus of claim 8, wherein the filter part is inside the filter, the filter part having a center spaced apart from a central axis of the inner space, and
the transmissive part having a center on the central axis of the inner space, and the transmissive part configured to surround the filter.

10. The substrate inspection apparatus of claim 1, further comprising:
a controller configured to,
control the light source,
the light adjuster,
perform a first inspection process and a second inspection process, and
extract information on the defect based on the generated scattering signal collected by the light adjuster,
wherein,
the light source includes,
a first light source configured to emit a first incident light towards the substrate, and
a second light source configured to emit a second incident light towards the light adjuster, and
the controller is further configured to,
emit the first incident light to the substrate during the first inspection process, and
emit the second incident light to the light adjuster during the second incident inspection process.

11. The substrate inspection apparatus of claim 10, wherein the controller is further configured to,
determine whether there is a first region within the defect during the first inspection process, the first region is an abnormal region which includes a size larger than a desired size, and
perform the second inspection process on a second region of the substrate, the second region is different from the abnormal region.

12. A substrate inspection apparatus, comprising:
a support configured to support a substrate;
a light source configured to emit an incident light towards an inspection region of the substrate;
a light adjuster including a reflector, the reflector positioned over the inspection region, and the reflector configured to allow the incident light to be substantially totally reflected;
a detector configured to collect a first scattering signal, the first scattering signal generated based on an optical interaction between an evanescent wave and a defect on the inspection region, the evanescent wave generated when the incident light is reflected; and a controller configured to, control the support, the light source, the light adjuster, and the detector, wherein the light adjuster and the substrate are separated from each other by a distance, the distance is a reachable distance for the evanescent wave, perform a first inspection process and a second inspection process, the first inspection process is performed before the second inspection process, irradiate the inspection region with the incident light and collect a second scattering signal generated from an optical interaction between the incident light and the defect during the second inspection process, and irradiate the reflector with the incident light and collect the first scattering signal during the second inspection process.

13. The substrate inspection apparatus of claim 12, wherein the controller is further configured to, determine whether there is a first region within the defect, the first region is an abnormal region which includes a size larger than a desired size based on the second scattering signal, and control the detector to exclude the abnormal region from the inspection region during the second inspection process.

14. A substrate inspection apparatus comprising:

a light source configured to emit an incident light;

a support configured to support a substrate;

a detector configured to detect a defect on the substrate based on a generated scattering signal received by the detector; and a light adjuster configured to substantially totally reflect the incident light, the generated scattering signal is generated based on an optical interaction between an evanescent wave and the defect on the substrate, the evanescent wave is generated when the incident light is reflected by the light adjuster, wherein the light adjuster comprises a light-condenser configured to reflect the incident light within the light-condenser; and a filter configured to remove a reflected fraction of the incident light, wherein the filter comprises a transmissive part configured to have the incident light incident into an inner space of the light adjuster; and a filter part configured to limit propagation of the reflected fraction from the inner space to the light adjuster.

15. The substrate inspection apparatus of claim 14, further comprising:

a controller configured to, control the light source, the light adjuster, perform a first inspection process and a second inspection process, and extract information on the defect based on the generated scattering signal collected by the light adjuster, wherein, the light source includes, a first light source configured to emit a first incident light towards the substrate, and a second light source configured to emit a second incident light towards the light adjuster, and the controller is further configured to, emit the first incident light to the substrate during the first inspection process, and emit the second incident light to the light adjuster during the second incident inspection process.

16. The substrate inspection apparatus of claim 15, wherein the controller is further configured to, determine whether there is a first region within the defect during the first inspection process, the first region is an abnormal region which includes a size larger than a desired size, and perform the second inspection process on a second region of the substrate, the second region is different from the abnormal region.

17. The substrate inspection apparatus of claim 14, wherein the light adjuster is between the detector and the substrate.

18. The substrate inspection apparatus of claim 17, wherein the light adjuster and a top surface of the substrate are separated from each other by a distance, and the evanescent wave is configured to reach the top surface but not pass through the top surface.

19. The substrate inspection apparatus of claim 18, wherein a range of the distance is from 150 nm (nanometer) to 300 nm.

* * * * *